United States Patent [19]

Rasberger et al.

[11] 4,321,218

[45] Mar. 23, 1982

[54] PHOSPHITE STABILIZER

[75] Inventors: Michael Rasberger, Riehen; Helmut Müller, Binningen, both of Switzerland

[73] Assignee: Ciba-Geigy Corporation, Ardsley, N.Y.

[21] Appl. No.: 145,072

[22] Filed: Apr. 30, 1980

Related U.S. Application Data

[63] Continuation of Ser. No. 974,187, Dec. 28, 1978, abandoned.

[30] Foreign Application Priority Data

Jan. 10, 1978 [CH] Switzerland .......................... 224/78

[51] Int. Cl.³ .......................... C07F 9/145; C08K 5/52
[52] U.S. Cl. .................................... 260/967; 524/151
[58] Field of Search .......................... 260/45.7 PH, 967

[56] References Cited

U.S. PATENT DOCUMENTS

| | | | |
|---|---|---|---|
| 2,058,343 | 10/1936 | Moran et al. | 252/49.8 |
| 2,220,845 | 11/1940 | Moyle | 260/967 |
| 2,733,226 | 1/1956 | Hunter | 260/45.7 PH |
| 3,231,531 | 1/1966 | Buckley et al. | 260/45.75 W |
| 3,244,661 | 4/1966 | Kline | 260/45.7 PH |
| 3,305,520 | 2/1967 | Fritz et al. | 260/45.7 PH |
| 3,322,718 | 5/1967 | Jacob | 260/45.7 PH |
| 3,373,210 | 3/1968 | Nishio et al. | 568/793 |
| 3,419,523 | 12/1968 | Herbstman | 260/45.7 PS |
| 3,533,989 | 10/1970 | Wescott, Jr. | 260/45.7 PH |
| 3,558,554 | 1/1971 | Kuriyama et al. | 260/45.7 PH |
| 3,960,758 | 6/1976 | Witte et al. | 260/45.95 C |
| 4,187,212 | 2/1980 | Zinke et al. | 260/45.8 NT |
| 4,196,117 | 4/1980 | Spivack | 260/45.7 PH |

*Primary Examiner*—John Kight, III
*Assistant Examiner*—R. A. White
*Attorney, Agent, or Firm*—Luther A. R. Hall; Vincent J. Cavalieri

[57] ABSTRACT

Tris-(2,4-di-t-octylphenyl)-phosphite is suitable as a stabilizer for organic material.

1 Claim, No Drawings

PHOSPHITE STABILIZER

This is a continuation of application Ser. No. 974,187, filed on Dec. 28, 1978, now abandoned.

The present invention relates to a novel alkylated triarylphosphite, to its use as a stabiliser and costabiliser against thermooxidative and light-induced degradation of organic material, and also to the organic material stabilised with this novel alkylated and triarylphosphite.

The esters of phosphorous acid are of importance for stabilising organic material, and have frequently been described in the literature. Thus the use of symmetrical alkylated triarylphosphites in polyolefines is known for example from the German Offenlegungsschrift No. 2,606,358.

There has now been found a novel triarylphosphite which better satisfies the strict requirements that a stabiliser has to meet than do known compounds. The novel substance is characterised in particular in that it has combined within it the widest range of valuable properties, such as high storage stability, stability to hydrolysis and resistance to extraction and a good stabilising action with excellent colouring properties, low volatility and good compatibility and emulsifiability. The compound according to the invention is tris-(2,4-di-t-octylphenyl)-phosphite:

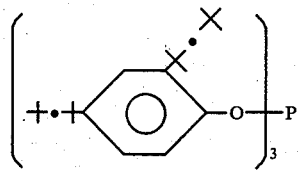

Although this novel phosphite displays it best features during the processing of polymers, it is also suitable as a long-term stabiliser, especially when it is employed together with other stabilisers in synergistic mixtures.

Tris-(2,4-di-t-octylphenyl)-phosphite is produced by methods known per se, for example by reaction of approximately three mols of 2,4-di-t-octylphenol with approximately one mol of phosphorus trichloride without solvent at 20°–250° C., or in an inert aprotic solvent, optionally in the presence of an organic base. Suitable inert solvents are chlorinated hydrocarbons such as chloroform, or preferably aromatic hydrocarbon compounds such as xylene, toluene or benzene. The reaction temperature is governed by the solvent, and can be from 20° C. to the reflux temperature. Suitable organic bases are in particular organic amines such as triethylamine or pyridine. It is also possible to use the organic base itself as solvent. A further method comprises reacting approximately three mols of 2,4-di-t-octylphenol with approximately one mol of triphenylphosphite, preferably without solvent, in the presence of a basic catalyst, such as sodium ethylate, sodium amide or lithium butyrate.

Tris-(2,4-di-t-octylphenyl)-phosphite is suitable for stabilising organic material, for example:

1. Polymers which are derived from singly or doubly unsaturated hydrocarbons, such as polyolefines, for example polyethylene which can optionally be crosslinked, polypropylene, polyisobutylene, polymethylbutene-1, polymethylpentene-1, polyisoprene, polybutadiene, polyisobutylene.

2. Mixtures of the homopolymers mentioned under (1), for example mixtures of polypropylene and polyethylene, polypropylene and polybutene-1, and polypropylene and polyisobutylene.

3. Copolymers of the monomers on which the homopolymers mentioned under (1) are based, such as ethylene/propylene copolymers, propylene butene copolymers, propylene/isobutylene copolymers, ethylene/butene-1 copolymers, and terpolymers of ethylene and propylene with a diene, such as hexadiene, dicyclopentadiene or ethylidenenorbornene.

4. Polystyrene.

5. Copolymers of styrene as well as of α-methylstyrene, such as styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to obtain high impact strength, and also styrene polymers modified with EPDM to obtain high impact strength.

6. Graft copolymers of styrene, such as styrene on polybutadiene, styrene and acrylonitrile on polybutadiene, and mixtures thereof with the copolymers mentioned under (5), generally known as acrylonitrile/butadiene/styrene or ABS plastics.

7. Halogen-containing vinyl polymers, such as polyvinyl chloride, polyvinylidene chloride, polyvinyl fluoride, polychloroprene, chlorinated rubbers, vinyl chloride/vinylidene chloride copolymers, vinyl chloride/vinyl acetate copolymers or vinylidene chloride/vinyl acetate copolymers.

8. Polymers which are derived from α,β-unsaturated acids and derivatives thereof, polyacrylates and polymethacrylates, polyacrylamides and polyacrylonitrile.

9. Polymers which are derived from unsaturated alcohols and amines or acyl derivatives or acetals thereof, such as polyvinyl alcohol, polyvinyl acetate, polyvinyl stearate, polyvinyl benzoate, polyvinyl maleate, polyvinyl butyrate, polyallyl phthalete, polyallyl-melamine and copolymers thereof with other vinyl compounds, such as ethylene/vinyl acetate copolymers.

10. Homopolymers and copolymers derived from epoxides, such as polyethylene oxide, or the polymers derived from bisglycidyl ethers.

11. Polyacetals, such as polyoxymethylene, and those polyoxymethylenes which as comonomers contain ethylene oxide.

12. Polyalkylene oxides, such as polyoxyethylene, polypropylene oxide or polyisobutylene oxide.

13. polyphenylene oxides.

14. Polyurethanes and polyureas.

15. Polycarbonates.

16. Polysulfones.

17. Polyamides and copolyamides which are derived from diamines and dicarboxylic acids and/or from aminocarboxylic acids or the corresponding lactams, such as polyamide 6, polyamide 6/6, polyamide 6/10, polyamide 11 or polyamide 12.

18. Polyesters which are derived from dicarboxylic acids and dialcohols and/or from hydroxycarboxylic acids or the corresponding lactones, such as polyethylene glycol terephthalate or poly-1,4-dimethylolcyclohexaneterephthalate.

19. Crosslinked polymers which are derived from aldehydes on the one hand and from phenols, ureas and melamines on the other hand, such as phenol/formaldehyde resins, urea/formaldehyde resins and melamine/formaldehyde resins.

20. Alkyd resins, such as glycerol/phthalic acid resins and mixtures thereof with melamine/formaldehyde resins.

21. Unsaturated polyester resins which are derived from copolyesters of saturated and unsaturated dicarboxylic acids with polyhydric alcohols and vinyl compounds as crosslinking agents, and also the halogen-containing difficultly combustible modifications thereof.

22. Natural polymers, such as cellulose, rubber, proteins and derivatives thereof which are chemically modified in a polymer-homologous manner, such as cellulose acetates, cellulose propionates and cellulose butyrates, or cellulose ethers, such as methylcellulose.

23. Natural and synthetic organic substances which are pure monomeric compounds or mixtures of such compounds, for example mineral oils, animal and plant fats, oils and waxes, or oils, waxes and fats based on synthetic esters, and mixtures of synthetic esters with mineral oils in any desired weight ratio.

Tris-(2,4-di-t-octylphenyl)-phosphite is incorporated, into the substrates, at a concentration of 0.005 to 5 percent by weight, relative to the material to be stabilised.

Preferably, 0.01 to 1.0, particularly preferably 0.02 to 0.5, percent by weight of the compounds, relative to the material to be stabilised, is incorporated into this material. Incorporation can be effected for example by mixing tris-(2,4-di-t-octylphenyl)-phosphite and optionally further additives into the melt by methods customary in the art, before or during moulding; or by application of the dissolved or dispersed compounds to the polymers, optionally with subsequent removal of the solvent by evaporation.

The novel compounds can be added, to the plastics being stabilised, also in the form of a master batch containing these compounds for example at a concentration of 2.5 to 25 percent by weight.

In the case of crosslinked polyethylene, the compounds are added before crosslinking.

The materials stabilised in the manner described can be applied in the most varied forms, for example in the form of sheets, fibres, tapes, moulding compounds or profiles, or as binders for lacquers, adhesives or cements.

In practice, tris-(2,4-di-t-octylphenyl)-phosphite can be used together with other stabilisers, and the result of this can be that synergistic mixtures are obtained. The present invention relates therefore also to the organic materials, which can optionally contain further additives, stabilised by the addition of 0.005 to 0.5 percent by weight of tris-(2,4-di-t-octylphenyl)-phosphite.

The combination of the phosphite according to the invention with a phenolic antioxidant is particularly preferred.

The following are to be mentioned as examples of phenolic compounds:

1. Simple 2,6-dialkylphenols, such as 2,6-di-tert-butyl-4-methylphenol, 2,6-di-tert-butyl-4-methoxymethylphenol or 2,6-di-tert-butyl-4-methoxyphenol;

2. Bisphenols, such as 2,2'-methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 1,1-bis-(5-tert-butyl-4-hydroxy-2-methylphenyl)-butane, 2,2-bis-(5-tert-butyl-4-hydroxy-2-methylphenyl)-butane, 2,2-bis-(3,5-di-tert-butyl-4-hydroxyphenyl)-propane, 1,1,3-tris-(5-tert-butyl-4-hydroxy-2-methylphenyl)-butane, 2,2-bis-(5-tert-butyl-4-hydroxy-2-methylphenyl)-4-n-dodecylmercapto-butane, 1,1,5,5-tetra-(5-tert-butyl-4-hydroxy-2-methylphenyl)-pentane, ethylene glycol-bis-[3,3-bis-(3'-tert-butyl-4'-hydroxyphenyl)-butyrate], 1,1-bis-(3,5-dimethyl-2-hydroxyphenyl)-3-(n-dodecylthio)-butane or 4,4'-thio-bis-(6-tert-butyl-3-methylphenol).

3. Hydroxybenzyl aromatics, such as 1,3,5-tri-(3,5-di-tert-butyl-4-hydroxybenzyl)-2,4,6-trimethylbenzene; 2,2-bis-(3,5-di-tert-butyl-4-hydroxybenzyl)-malonic acid dioctadecyl ester; 1,3,5-tris-(3,5-di-tert-butyl-4-hydroxybenzyl)-isocyanurate or 3,5-di-tert-butyl-4-hydroxybenzyl-phosphonic acid diethyl ester.

4. Amides of β-(3,5-di-tert-butyl-4-hydroxyphenyl)-propionic acid, such as 1,3,5-tris-(3,5-di-tert-butyl-4-hydroxyphenyl-propionyl)-hexahydro-s-triazine and N,N'-di-(3,5-di-tert-butyl-4-hydroxyphenyl-propionyl)-hexamethylenediamine.

5. Esters of β-(3,5-di-tert-butyl-4-hydroxyphenyl)-propionic acid with mono- or polyhydric alcohols, such as methanol, octadecanol, 1,6-hexanediol, ethylene glycol, thiodiethylene glycol, neopentyl glycol, pentaerythritol and tris-hydroxyethyl-isocyanurate.

6. Spiro compounds, such as diphenolic spiro-diacetals or spiro-diketals, such as 2,4,8,10-tetraoxaspiro-[5,5]-undecane substituted in the 3-, 9-position with phenolic radicals, for example 3,9-bis-(3,5-di-tert-butyl-4-hydroxyphenyl)-2,4,8,10-tetraoxaspiro-[5,5]-undecane and 3,9-bis-[1,1-dimethyl-2-(3,5-di-tert-butyl-4-hydroxyphenyl)-ethyl]-2,4,8,10-tetraoxaspiro-[5,5]-undecane.

Particularly preferred phenolic compounds are:
1,3,5-tri-(3,5-di-tert-butyl-4-hydroxybenzyl)-2,4,6-trimethylbenzene;
pentaerythritol-tetra-[3-(3,5-di-tert-butyl-4-hydroxyphenyl)-propionate];
β-(3,5-di-tert-butyl-4-hydroxyphenyl)-propionic acid-n-octadecyl ester;
thiodiethylene glycol-β-[4-hydroxy-3,5-di-tert-butylphenyl]-propionate;
2,6-di-tert-butyl-4-methyl-phenol;
1,1,3-tris-(5-t-butyl-4-hydroxy-2-methylphenyl)-butane;
2,2'-methylene-bis-(6-t-butyl-4-methylphenol);
4,4'-thio-bis-(6-t-butyl-3-methylphenol);
ethylene glycol-bis-(3,3-bis-3'-t-butyl-4'-hydroxyphenyl)-butyrate;
1,3,5-tris-(3',5'-di-t-butyl-4-hydroxybenzyl)-isocyanurate,
1,1-bis-(2'-methyl-4'-hydroxy-5'-t-butylphenyl)-butane.

The triarylphosphite and the phenolic antioxidant are incorporated in the ratio of 10:1 to 1:5, preferably 5:1 to 1:2, and in particular 3:1 to 1:1.

The following are to be mentioned as examples of further additives which can be used together with the phosphite according to the invention:

UV absorbers and light stabilisers, such as 2-(2'-hydroxyphenyl)-benzotriazoles, 2,4-bis-(2'-hydroxyphenyl)-6-alkyl-s-triazines, 2-hydroxybenzophenones, 1,3-bis-(2'-hydroxybenzoyl)-benzenes, esters of unsubstituted or substituted benzoic acids, acrylates, also nickel compounds, sterically hindered amines, oxalic acid diamides, metal deactivators, compounds which break down peroxide, polyamide stabilisers, thioethers, basic Co-stabilisers, nucleating agents, or other additives, for example plasticisers, lubricants, emulsifiers, fillers, carbon black, asbestos, kaolin, talc, glass fibres, pigments, optical brighteners, flameproofing agents or antistatic agents.

The invention is further illustrated by the following Examples.

EXAMPLE 1

21.2 g (0.21 mol) of triethylamine is added to 68.1 g (0.214 mol) of 2,4-di-t-octylphenol in 150 ml of xylene. There is then added dropwise during one hour, at room temperature, 9.6 g (0.07 mol) of phosphorus trichloride, and the mixture is held at 140° C. for 12 hours. The triethylamine hydrochloride is separated, and the solvent is evaporated off in vacuo. The tris-(2,4-di-t-octylphenyl)-phosphite remaining behind has a melting point of 120°–121° C. and gives the following elementary analysis:

| | | |
|---|---|---|
| calculated: | C 80.58% | H 11.36% |
| found: | C 80.6% | H 11.6%. |

EXAMPLE 2

500 mg of tris-(2,4-di-t-octylphenyl)-phosphite is placed into a small cylindrical flask (diameter 2 cm) in order to ensure a defined surface area. This flask is inserted into a larger flask of the same kind (diameter 7 cm), which contains glass balls up to the height of 3 cm and water up to the height of 1.5 cm in order to guarantee a moist atmosphere. The system is sealed and heated in an oven for 5 hours at 70° C. and 80° C., respectively. The increase in weight of the smaller flask serves as a measure of the water absorption.

Degradation of the compound caused by hydrolysis is ascertained by observation of the thin-layer chromatogram, with 2,4-di-t-octylphenol as a typical hydrolysis degradation product being used as a reference substance.

TABLE 1

| | 5 h/70° C. | 5 h/80° C. |
|---|---|---|
| increase in weight | 0% | 0.2% |
| chromatogram | identical with starting product | very slight hydrolysis perceptible |

As a typical triaromatic phosphite commercial product, tris-(nonylphenyl)-phosphite exhibits under identical test conditions an increase in weight of ~10% caused by water absorption, and is almost completely hydrolysed.

EXAMPLE 3

100 parts of unstabilised polyethylene of high density having a molecular weight of about 500,000 are dry mixed in each case with 0.1 part of tris-(2,4-di-tert-octylphenyl)-phosphite and 0.05 part of one of the antioxidants listed in the following Table. The mixtures are kneaded in a Brabender plastograph at 220° C. and 50 rpm for 20 minutes. During this time, the resistance to kneading is continuously recorded as a turning moment. In consequence of crosslinking of the polymer, there occurs in the course of the kneading operation, after an initial period of constant value, a rapid increase of the turning moment. The effectiveness of the stabilisers is manifested by a lengthening of the period of constant value of the turning moment. The comparison mixtures without tris-(2,4-tert-octylphenyl)-phosphite are produced in an analogous manner.

| Phenolic antioxidant | Time until turning moment increases |
|---|---|
| pentaerythritol-tetra-[3-(3,5-ditert-butyl-4-hydroxyphenyl)-propionate] | 8 min. |
| 1,3,5-tris-(3',5'-ditert-butyl-4-hydroxybenzyl)-isocyanate | 5.5 min. |
| 1,3,5-trimethyl-2,4,6-tris-(3',5'-ditert-butyl-4'-hydroxybenzyl)-benzene | 8 min. |

EXAMPLE 4

100 parts of polycarbonate powder are dry mixed with 0.1 part of tris-(2,4-di-tert-octylphenyl)-phosphite. The mixture is dried during 4 hours at 120° C.; it is then extruded in a single screw extruder at a maximum of 280° C., and granulated. The granules are dried as above and subsequently injection moulded at a maximum of 310° C. in an anchor injection-extrusion automatic machine into the form of 2 mm thick plates. The comparison plates without additive are produced in an analogous manner. Whereas the material without additive clearly tends to yellow during production of the plates, the plates containing the phosphite according to the invention remain practically colourless. The Yellowness Index according to ASTM D 1925-70 is used to quantify the impression of yellowness:

| | Yellowness Index |
|---|---|
| control specimen | 3.0 |
| with additive as described above | 0.9 |

EXAMPLE 5

100 Parts of commercial polyethylene terephthalate powder (without titanium dioxide) are mixed together with 0.2 part of tris-(2,4-di-tert-octylphenyl)-phosphite. The mixture is dried at 120° C. for 4 hours, and subsequently melted down at 275° C. under nitrogen for 30 minutes with stirring. The melt regulus obtained is ground with dry ice in a cross beater mill and then screened. The resulting powder is subjected to differential thermoanalysis (apparatus: Mettler TM 2000 A) with a heating-up rate of 5° C/min. The test is firstly performed under nitrogen, and then repeated in air. Whereas in the test under nitrogen there is observed only a melt endotherm at about 255° C., there are observed in the test in air oxidation effects (exothermic), which partially superimpose the melt endotherm. The values below signify temperatures at the commencement of the oxidation exotherm (Tox).

| | Tox (°C.) |
|---|---|
| control specimen | 208 |
| with additive as described above | 244 |

EXAMPLE 6

Unstabilised ABS latex is coagulated by the addition of dilute hydrochloric acid; the ABS which has precipitated is filtered off, washed with water and dried at 60° C. under nitrogen. 0.25 part of octadecyl-3-(3,5-ditertbutyl-4-hydroxyphenyl)-propionate and 0.5 part of tris-(2,4-di-tert-octylphenyl)-phosphite are dissolved in a mixture of cyclohexane and toluene. The solution is mixed with 100 parts of the dried ABS powder, and the solvent is subsequently carefully evaporated off. The dry ABS is again homogenised in a mixer. The comparison mixtures (antioxidant only, or without additive) are produced in the same manner.

The testing of the effectiveness of the applied additives is carried out by isothermal differential thermoanalysis at 170° C. (apparatus: Mettler TM 2000 A). The values below signify induction times until the occurrence of an exothermic maximum.

|  | Induction times in minutes |
|---|---|
| control specimen | <5 |
| 0.25% of octadecyl-3-(3,5-ditert-butyl-4-hydroxyphenyl)-propionate | 25 |
| 0.25% of octadecyl-3-(3,5-ditert-butyl-4-hydroxyphenyl)-propionate + 0.5% of tris-(2,4-ditert-octylphenyl)-phosphite | 41 |

EXAMPLE 7

Unstabilised ABS latex is coagulated by the addition of dilute hydrochloric acid. 0.25 part of octadecyl-3-(3,5-ditert-butyl-4-hydroxyphenyl)-propionate and 0.5 part of tris-(2,4-ditert-octylphenyl)-phosphite are dissolved in a mixture of cyclohexane and toluene. The solution is mixed together with the coagulated latex (amount corresponding to 100 parts of ABS solid substance), in the process of which the solution is quantitatively absorbed onto the ABS. After thorough stirring, the mixture is filtered and the residue is dried at 80° C. in vacuo. After the addition of 2 parts of titanium dioxide, additives and pigment are incorporated on a two-roller mill (temperature: 165/180° C.; 16/18 rpm). Plates having a thickness of 0.8 mm are pressed out from the rolled sheet. The comparison mixtures (antioxidant only, or without additive) are produced in an analogous manner.

The testing of the effectiveness of the incorporated additives is carried out by oven ageing at 180° C. The degree of yellowing during oven ageing after 30 minutes serves as a typical test criterium for ABS. The Yellowness Index according to ASTM D 1925-70 is used to quantify the impression of yellowness.

|  | Yellowness Index |
|---|---|
| control specimen | 55 |
| 0.25% of octadecyl-3-(3,5-ditert-butyl-4-hydroxyphenyl)-propionate | 43 |
| 0.25% of octadecyl-3-(3,5-ditert-butyl-4-hydroxyphenyl)-propionate + 0.5% of tris-(2,4-ditert-octylphenyl)-phosphite | 27 |

EXAMPLE 8

100 parts of commercial granules produced from impact resistant polystyrene (containing as basic stabilisation 0.03% of 2,6-ditert-butyl-p-cresol) are mixed with 0.1 part of octadecyl-3-(3,5-ditert-butyl-4-hydroxyphenyl)-propionate, 0.1 part of tris-(2,4-ditert-octylphenyl)-phosphite and 0.2 part of zinc stearate. The additives are incorporated on a two-roller mill (temperature: 150/160° C.; 16/18 rpm; 4 minutes). Plates having a thickness of 0.8 mm are pressed out from the rolled sheet. The comparison mixtures (antioxidant only, or without additive) are produced in the same manner.

The testing of the effectiveness of the incorporated additives is carried out by oven ageing at 80° C. The yellowing during oven ageing after 2000 hours serves as a typical test criterium for impact resistant polystyrene. The Yellowness Index according to ASTM D-1925-70 is used to quantify the impression of yellowness:

|  | Yellowness Index |
|---|---|
| control specimen | 75 |
| 0.1% of octadecyl-3-(3,5-ditert.butyl-4-hydroxyphenyl)-propionate | 46 |
| 0.1% of octadecyl-3-(3,5-ditert-butyl-4-hydroxyphenyl)-propionate + 0.1% of tris-(2,4-ditert-octylphenyl)-phosphite | 34 |

What is claimed is:
1. Tris-(2,4-di-t-octylphenyl)-phosphite.

* * * * *